United States Patent
Farber (12)

(10) Patent No.: US 6,281,236 B1
(45) Date of Patent: Aug. 28, 2001

(54) OIL-IN-WATER EMULSION WITH IMPROVED STABILITY

(75) Inventor: Elliott Farber, North Mankato, MN (US)

(73) Assignee: Alwyn Company, Inc., Lake Crystal, MN (US)

( * ) Notice: Subject to any disclaimer, the term of this patent is extended or adjusted under 35 U.S.C. 154(b) by 0 days.

(21) Appl. No.: 09/360,095

(22) Filed: Jul. 23, 1999

(51) Int. Cl.[7] ............................. A61K 9/107; A61K 7/00; A61K 9/113; A61K 31/4166; A61K 31/4168

(52) U.S. Cl. ..................... 514/390; 424/401; 424/405; 424/70.22; 424/70.23; 424/70.24; 424/70.31; 424/730; 424/725; 514/937; 514/939; 514/940; 514/941; 514/943

(58) Field of Search ........................ 424/401, 405, 424/70.22, 70.24, 70.23, 70.31, 725, 730; 514/390, 937, 939, 940, 941, 943

(56) References Cited

U.S. PATENT DOCUMENTS

| | | | |
|---|---|---|---|
| 3,830,824 | 8/1974 | Margraf | 260/299 |
| 3,830,825 | 8/1974 | Margraf | 260/299 |
| 3,830,908 | 8/1974 | Klippel et al. | 424/28 |
| 3,856,805 | 12/1974 | Margraf | 260/299 |
| 3,930,000 | 12/1975 | Margraf | 424/245 |
| 3,932,627 | 1/1976 | Margraf | 424/183 |
| 3,954,989 | 5/1976 | Mecca | 424/273 |
| 4,170,229 | 10/1979 | Olson . | |
| 4,278,664 | 7/1981 | Van Cleave . | |
| 4,374,766 | 2/1983 | Puchalski et al. | 260/123.7 |
| 4,670,263 | 6/1987 | Noorlander | 424/195.1 |
| 4,707,354 | 11/1987 | Garlen et al. . | |
| 4,708,813 | 11/1987 | Snyder . | |
| 4,806,262 | 2/1989 | Snyder . | |
| 4,981,845 | 1/1991 | Pereira . | |
| 5,112,886 | 5/1992 | Phalangas . | |
| 5,122,533 | 6/1992 | Bar-On et al. . | |
| 5,221,533 | 6/1993 | Perlman | 424/73 |
| 5,455,033 | 10/1995 | Silverman et al. | 424/195 |
| 5,512,200 | 4/1996 | Garcia | 252/142 |
| 5,567,427 | 10/1996 | Papadakis . | |
| 5,658,559 | 8/1997 | Smith . | |
| 5,661,170 | 8/1997 | Chodosh . | |
| 5,736,128 | 4/1998 | Chaudhuri et al. . | |
| 5,824,666 | 10/1998 | Deckner et al. | 514/152 |
| 5,827,870 | 10/1998 | Chodosh . | |
| 5,863,548 | 1/1999 | Elder | 424/408 |
| 5,871,754 | 2/1999 | Briggs et al. . | |
| 5,885,581 | 3/1999 | Massand | 424/195.1 |
| 5,914,116 | 6/1999 | Suares et al. | 424/401 |
| 5,932,228 | 8/1999 | Hall et al. | 424/401 |
| 5,952,373 | 9/1999 | Lanzendörfer et al. | 514/456 |
| 5,958,436 | 9/1999 | Hahn et al. | 424/401 |
| 6,060,061 | 5/2000 | Breton et al. | 424/195.1 |
| 6,080,393 * | 6/2000 | Liu et al. | 424/78.03 |

FOREIGN PATENT DOCUMENTS

| | | | |
|---|---|---|---|
| 030157 | 8/1990 | (EP) | A61K/33/04 |
| 0242553 | 10/1997 | (EP) | A61K/33/04 |
| WO 90/09779 | 9/1990 | (WO) | A61K/7/16 |

OTHER PUBLICATIONS

Remington: Science and Practice of Pharmacy, vol. (1), p. 639–641, 1995.*
David Hoffmann *The complete Illustrated Herbal,* Element Books, p. 63, 104, 1996.*
publication—product information insert for Alphosyl Cream and Alphosyl Lotion, G.D. Searle (South Africa), Apr. 24, 1975.
publication—product information insert for Clearasil Medicated Facial Cleanser, Procter & Gamble (South Africa), Jan. 31, 1994.
publication—product information insert for Arola Rosebaum, Supramed Limited, Jan. 12, 1986.
abstract of a publication—M. Cajkovac et al., "Influence of Emulsoid Vehicle on the Release and Activity of Allantoin," *Pharmazie* 47: 39–43 (1992).
abstract of a publication—M. Maragakis et al., "Possibilities of Scar Treatment After Thoracic Surgery," *Drugs Under Exp. & Clin. Res.* 21: P199–206 (1995).
product information insert for Alphosyl, undated.
abstract of a publication—G. Stinco et al., "Seborrheic Dermatitis Treated with Furalglucitole Cream," *Dermatol. Clin.* 18: 78–81 (1998).
abstract of a publication—M. Maragakis et al., "Possibilities of Scar Treatment After Thoracic Surgery," *Drugs Exp. Clin.Res.* 21: 199–206 (1999).
abstract of a publication—G.H. Willital & H. Heine, "Efficiency of Contractubex® Gel in the Treatment of Fresh Scars After Thoracic Surgery in Children and Adolescents," *Int. J. Clin. Pharmacol. Res.* 14: 193–202 (1994).
publication—H.W. Margraf & T.H. Covey, Jr., "A Trial of Silver–Zinc–Allantoinate in the Treatment of Leg Ulcers," *Arch. Surg.* 12: 699–704 (1977).

* cited by examiner

*Primary Examiner*—Diana Dudash
*Assistant Examiner*—S Sharareh
(74) *Attorney, Agent, or Firm*—Oppenheimer, Wolff & Donnelly, LLP

(57) ABSTRACT

A skin cream composition containing allantoin and an emulsifier has improved stability coming from the adjustment of the pH to a range of 4.5 to 5.8. The lower pH preserves the stability of the allantoin and the functionality of the emulsifier system is maintained. The emulsifier system can be a nonionic emulsifier or an anionic emulsifier plus beeswax. The acid used to adjust the pH can be an organic acid or an inorganic acid. The composition can further comprise other ingredients such as herbal extracts, chelating agents, preservatives, emollients, solvents, and fragrance.

48 Claims, No Drawings

OIL-IN-WATER EMULSION WITH IMPROVED STABILITY

BACKGROUND OF THE INVENTION

This invention is directed to oil-in-water emulsions in which allantoin has improved stability, particularly for cosmetic and over-the-counter drug applications.

Allantoin is a commonly used ingredient in cosmetic applications, particularly for skin creams, where it exerts a skin protective function. Many such cosmetic compositions are prepared as emulsions, particularly oil-in-water emulsions. One emulsifier system used with such compositions is a combination of sodium lauryl sulfate and beeswax. Although solutions of sodium lauryl sulfate are alkaline with an approximate pH of 9.5, the simultaneous use of beeswax with its organic acids produces a complex and neutralized system with a pH of about 6.8 to about 7.5. However, in such a system with a pH range of 6.8 to 7.5, allantoin degrades significantly with time in an accelerated stability test at 40° C. Because cosmetics are typically stored by users at room temperature, and room temperatures can fluctuate with climatic conditions, such a degree of instability is undesirable. Therefore, there is a need for an oil-in-water emulsified composition containing allantoin that uses the sodium lauryl sulfate-beeswax emulsion system in which the stability of allantoin is increased.

SUMMARY

An improved composition containing allantoin uses an emulsification system in which the pH is adjusted to from about 4.5 to about 5.8 with the use of a small amount of acid.

The emulsification system can include beeswax and an anionic emulsifier that is substantially hydrophilic and is soluble in water. Alternatively, the emulsification system can include a nonionic emulsifier that is an ethoxylated ether or an ethoxylated ester whose carbon chain length ranges from 8 to 22 carbon atoms.

One embodiment of a composition according to the present invention comprises:
(1) allantoin; and
(2) an emulsifier system including beeswax and an anionic emulsifier that is substantially hydrophilic and is soluble in water, the pH of the emulsion being from about 4.5 to about 5.8 after the addition of acid to bring the pH into the range.

The emulsifier can be selected from the group consisting of ammonium lauryl sulfate, sodium lauryl sulfate, sodium laureth sulfate, sodium oleyl succinate, ammonium lauryl sulfosuccinate, sodium dodecylbenzenesulfonate, ammonium laureth sulfate, and sodium lauryl sarcosinate. In one preferred embodiment, the emulsifier is sodium lauryl sulfate.

The composition can comprise at least one organic acid of from 2 to 22 carbon atoms. The organic acid can be citric acid, ascorbic acid, glycolic acid, lactic acid, benzoic acid, or salicylic acid. Alternatively, the composition can comprise at least one inorganic acid selected from the group consisting of hydrochloric acid, sulfuric acid, and phosphoric acid. The composition can comprise both organic and inorganic acids.

Another embodiment of a composition according to the present invention comprises an oil-in-water emulsion comprising:
(1) allantoin; and
(2) an emulsifier system including at least one nonionic emulsifier that is an ethoxylated ether or an ethoxylated ester whose carbon chain length ranges from 8 to 22 carbon atoms, the pH of the emulsion being from about 4.5 to about 5.8 after the addition of acid to bring the pH into the range.

The composition can further include a number of ingredients. These ingredients can include the following:
(1) an emollient component that is one or more of lanolin oil, cetyl alcohol, stearyl alcohol, cod liver oil, and butylated hydroxytoluene;
(2) herbal extracts, including one or more of St. John's wort extract, witch hazel extract, chamomile extract, and arnica extract;
(3) a preservative component that is one or more of methylparaben and propylparaben; and
(4) a solvent component that is one or more of propylene glycol, glycerol, or butylene glycol, and is preferably propylene glycol.

One preferred composition according to the present invention comprises:
(1) water;
(2) sodium lauryl sulfate;
(3) propylene glycol;
(4) tetrasodium EDTA;
(5) citric acid;
(6) lanolin oil;
(7) cetyl alcohol;
(8) stearyl alcohol;
(9) beeswax;
(10) cod liver oil;
(11) butylated hydroxytoluene;
(12) St. John's wort extract;
(13) witch hazel extract;
(14) chamomile extract;
(15) arnica extract;
(16) methylparaben;
(17) propylparaben;
(18) allantoin; and
(19) fragrance;
where the pH of the composition is from about 4.5 to about 5.8.

A more preferred composition according to the present invention comprises:
(1) from about 50% to about 90% of water;
(2) from about 0.5% to about 2.5% of 30% sodium lauryl sulfate;
(3) from about 2.0% to about 9.0% of propylene glycol;
(4) from about 0.05% to about 0.50% of tetrasodium EDTA;
(5) from about 0.05% to about 0.5% of citric acid;
(6) from about 5% to about 15% of lanolin oil;
(7) from about 3% to about 10% of cetyl alcohol;
(8) from about 1% to about 5% of stearyl alcohol;
(9) from about 0.5% to about 2.5% of beeswax;
(10) from about 1.0% to about 7.0% of cod liver oil;
(11) from about 0.1% to about 1.0% of butylated hydroxytoluene;
(12) from about 0.05% to about 0.50% of St. John's wort extract;
(13) from about 0.05% to about 0.50% of witch hazel extract;

(14) from about 0.05% to about 0.5% of chamomile extract;
(15) from about 0.05% to about 0.5% of arnica extract;
(16) from about 0.1% to about 0.5% of methylparaben;
(17) from about 0.1% to about 0.5% of propylparaben;
(18) from about 0.50% to about 2% of allantoin; and
(19) from about 0.05% to about 0.50% of fragrance;
the pH of the composition being from about 4.5 to about 5.8.

A still more preferred composition according to the present invention comprises:
(1) from about 55% to about 75% of water;
(2) from about 1.0% to about 2.5% of 30% sodium lauryl sulfate;
(3) from about 3.0% to about 6.0% of propylene glycol;
(4) from about 0.1% to about 0.3% of tetrasodium EDTA;
(5) from about 0.08% to about 0.35% of citric acid;
(6) from about 8.0% to about 12.0% of lanolin oil;
(7) from about 3.5% to about 7.5% of cetyl alcohol;
(8) from about 1.0% to about 3.0% of stearyl alcohol;
(9) from about 1.0% to about 2.5% of beeswax;
(10) from about 1.0% to about 4.0% of cod liver oil;
(11) from about 0.2% to about 0.8% of butylated hydroxytoluene;
(12) from about 0.05% to about 0.15% of St. John's wort extract;
(13) from about 0.05% to about 0.15% of witch hazel extract;
(14) from about 0.05% to about 0.15% of chamomile extract;
(15) from about 0.05% to about 0.15% of arnica extract;
(16) from about 0.15% to about 0.40% of methylparaben;
(17) from about 0.10% to about 0.30% of propylparaben;
(18) from about 0.50% to about 2.0% of allantoin; and
(19) from about 0.1% to about 0.3% of fragrance;
the composition having a pH of from about 4.5 to about 5.8.

A still more preferred composition according to the present invention comprises:
(1) about 68.68% of water;
(2) about 1.9% of 30% sodium lauryl sulfate;
(3) about 5.3% of propylene glycol;
(4) about 0.15% of tetrasodium EDTA;
(5) about 0.12% of citric acid;
(6) about 10.6% of lanolin oil;
(7) about 4.2% of cetyl alcohol;
(8) about 2.0% of stearyl alcohol;
(9) about 1.90% of beeswax;
(10) about 2.0% of cod liver oil;
(11) about 0.5% of butylated hydroxytoluene;
(12) about 0.1% of St. John's wort extract;
(13) about 0.1% of witch hazel extract;
(14) about 0.1% of chamomile extract;
(15) about 0.1% of arnica extract;
(16) about 0.3% of methylparaben;
(17) about 0.25% of propylparaben;
(18) about 1.50% of allantoin; and
(19) about 0.20% of fragrance;
the composition having a pH of from about 4.5 to about 5.8.

DESCRIPTION

An improved composition containing allantoin uses an emulsification system including either: (1) beeswax and an anionic emulsifier that is substantially hydrophilic or (2) a nonionic emulsifier that is an ethoxylated ether or an ethoxylated ester whose carbon chain length ranges from 8 to 22 carbon atoms, in which the pH is adjusted to from about 4.5 to about 5.8 with the use of a small amount of acid. As shown below in Example 4, the stability of allantoin at 40° C. is greatly improved while simultaneously maintaining the functionality of the emulsion system. This result is unexpected because acid can hydrolyze emulsifiers such as sodium lauryl sulfate.

Therefore, the present invention is directed to oil-in-water emulsions that include allantoin and an emulsifier system that includes either: (1) beeswax and an anionic emulsifier system or (2) a nonionic emulsifier system.

If the emulsifier system is a nonionic emulsifier system, the emulsifier typically comprises ethoxylated ethers or ethoxylated esters whose carbon chain lengths range from 8 to 22 carbon atoms.

If the emulsifier system includes anionic emulsifiers, the anionic emulsifiers are substantially hydrophilic and are soluble in water. The anionic emulsifier is typically one of ammonium lauryl sulfate, sodium laureth sulfate, sodium oleyl succinate, ammonium lauryl sulfosuccinate, sodium dodecylbenzenesulfonate, ammonium laureth, sodium N-lauryl sarcosinate, or sodium lauryl sulfate. A particularly preferred anionic emulsifier is sodium lauryl sulfate.

The composition further includes an acid to reduce the pH to a pH in a range from about 4.5 to about 5.8. The acid can be an organic acid, an inorganic acid, or a mixture of both.

Preferred organic acids include organic acids whose carbon chain length ranges from 2 to 22 carbon atoms and can be monocarboxylic, dicarboxylic, or tricarboxylic acids. The acids can be aliphatic or aromatic. Particularly preferred organic acids include citric acid, ascorbic acid, glycolic acid, lactic acid, benzoic acid, and salicylic acid. A most particularly preferred organic acid is citric acid.

Typically, the inorganic acid is a strong acid. It can be a monoprotic, diprotic, or triprotic acid. Particularly preferred inorganic acids include hydrochloric acid, sulfuric acid, and phosphoric acid.

The composition can further include other ingredients. For example, the composition can include an emollient component for smoothness. The emollient component can include at least one of lanolin oil, cetyl alcohol, stearyl alcohol, cod liver oil, and butylated hydroxytoluene. Preferably, the emollient component comprises all of lanolin oil, cetyl alcohol, stearyl alcohol, cod liver oil, and butylated hydroxytoluene.

The composition can further include a solvent component. Typically, the solvent component is one or more of propylene glycol, glycerin, or butylene glycol. Preferably, the solvent component is propylene glycol.

The composition can further include a chelating agent to bind metal ions that might accelerate degradation of the compound. A particularly preferred chelating agent is tetrasodium EDTA.

The composition can further include herbal extracts. The herbal extracts can include one or more of St. John's wort extract, witch hazel extract, chamomile extract, and arnica extract. Preferably, the composition includes all of St. John's wort extract, witch hazel extract, chamomile extract, and arnica extract.

The composition can further include a preservative such as methylparaben, ethylparaben, propylparaben, butylparaben, or phenoxyethanol. Preferably, the composition comprises methylparaben and propylparaben as preservatives.

The composition can further include fragrance. The use of fragrance is well known in the cosmetic art and in the art of over-the-counter drug formulation, and many suitable fragrances are known in the art. The stability and function of the cream is not altered by the presence or absence of fragrance.

The composition can further include other components, such as proteins, humectants, other preservatives, essential oils, other vitamins, colorants, hydroxyacids, other plant extracts, sunscreens, sodium hyaluronate, lipids, fatty acids, thickeners, panthenol, and the like. The use of such components is conventional in the cosmetic art and in the over-the-counter drug art. Typical sunscreens are octyl methoxycinnamate and benzophenone-3.

The following discussion describes ranges, preferred concentrations, and optimum concentrations for preferred compositions according to the present invention.

Water can comprise from about 50% to about 90% of the composition. Preferably, water comprises from about 55% to about 75% of the composition. An optimum concentration of water is about 68.68%.

Sodium lauryl sulfate, as a 30% solution, can comprise from about 0.5% to about 2.5% of the composition. Preferably, sodium lauryl sulfate comprises from about 1.0% to about 2.5% of the composition. An optimum concentration of sodium lauryl sulfate in the composition is about 1.9%.

Propylene glycol can comprise from about 2.0% to about 9.0% of the composition. Preferably, propylene glycol comprises from about 3.0% to about 6.0% of the composition. An optimum concentration of propylene glycol is about 5.3% of the composition.

Tetrasodium EDTA can comprise from about 0.05% to about 0.50% of the composition. Preferably, tetrasodium EDTA comprises from about 0.10% to about 0.30% of the composition. An optimum concentration of tetrasodium EDTA is 0.15% of the composition.

Citric acid can comprise from about 0.05% to about 0.50% of the composition. A preferred concentration of citric acid is from about 0.08% to about 0.35% of the composition. An optimum concentration of citric acid is about 0.12%.

Lanolin oil can comprise from about 5.0% to about 15.0% of the composition. Preferably, lanolin oil comprises from about 8.0% to about 12.0% of the composition. An optimum concentration of lanolin oil is about 10.60% of the composition.

Cetyl alcohol can comprise from about 3.0% to about 10.0% of the composition. A preferred concentration of cetyl alcohol is from about 3.5% to about 7.5% of the composition. An optimum concentration of cetyl alcohol is about 4.2% of the composition.

Stearyl alcohol can comprise from about 1.0% to about 5.0% of the composition. A preferred concentration of stearyl alcohol is from about 1.0% to about 3.0% of the composition. An optimum concentration of stearyl alcohol is about 2.0% of the composition.

Beeswax can comprise from about 0.5% of the composition to about 2.5% of the composition. A preferred concentration of beeswax is about 1.0% to about 2.5% of the composition. An optimum concentration of beeswax is about 1.9% of the composition.

Cod liver oil can comprise from about 1.0% to about 7.0% of the composition. Preferably, cod liver oil comprises from about 1.0% to about 4.0% of the composition. An optimum concentration of cod liver oil is about 2.0% of the composition.

Butylated hydroxytoluene can comprise from about 0.1% to about 1.0% of the composition. Preferably, butylated hydroxytoluene comprises from about 0.2% to about 0.8% of the composition. An optimum concentration of butylated hydroxytoluene is about 0.50% of the composition.

St. John's wort extract can comprise from about 0.05% to about 0.5% of the composition. Preferably, St. John's wort extract comprises from about 0.05% to about 0.15% of the composition. An optimum concentration of St. John's wort extract is about 0.10% of the composition.

Witch hazel extract can comprise from about 0.05% to about 0.5% of the composition. Preferably, witch hazel extract comprises from about 0.05% to about 0.15% of the composition. An optimum concentration of witch hazel extract is about 0.10% of the composition.

Chamomile extract can comprise from about 0.05% to about 0.50% of the composition. A preferred concentration of chamomile extract is from 0.05% to about 0.15% of the composition. An optimum concentration of chamomile extract is about 0.10% of the composition.

Arnica extract can comprise from about 0.5% to about 0.50% of the composition. Preferably, arnica extract comprises from about 0.05% to about 0.15% of the composition. An optimum concentration of arnica extract is about 0.10% of the composition.

Methylparaben can comprise from about 0.10% to about 0.50% of the composition. A preferred concentration of methylparaben is from 0.15% to about 0.40% of the composition. An optimum concentration of methylparaben is about 0.30% of the composition.

Propylparaben can comprise from about 0.10% to about 0.50% of the composition. Preferably, propylparaben comprises from about 0.10% to about 0.30% of the composition. An optimum concentration of propylparaben is about 0.25% of the composition.

Allantoin can comprise from about 0.50% to about 2.0% of the composition. A preferred concentration of allantoin is from about 0.50% to about 2.0% of the composition. An optimum concentration of allantoin is about 1.50% of the composition.

Fragrance can comprise from about 0.05% of the composition to about 0.50% of the composition. Preferably, fragrance comprises from about 0.10% of the composition to about 0.30% of the composition. An optimum concentration of fragrance is about 0.20% of the composition.

The composition is prepared by standard mixing techniques, such as are conventional in the cosmetic art for blending lipid-soluble components and water-soluble components. These mixing techniques include both manual and mechanical mixing, and include homogenization mixing and sweep mixing. The mixing techniques to be used can be chosen by one of ordinary skill in the art based on variables such as the viscosity of the components to be mixed and the volume of those components. Further details of preparation of the composition are described in Example 2.

The invention is illustrated by the following Examples. These examples are for illustrative purposes only and are not intended to limit the invention.

EXAMPLES

Example 1

Preparation of Skin Protectant Over-the-Counter Cream with pH of 7.4

(Prior Art Example)

A skin protectant over-the-counter (OTC) cream was prepared in accordance with the formulation of Table 1.

TABLE 1

COMPOSITION OF ALLANTOIN-CONTAINING SKIN CREAM WITH pH OF 7.4

| INGREDIENT | RANGE | PREFERRED | OPTIMUM |
|---|---|---|---|
| Part A | | | |
| Water | 50.0–90.0 | 55.0–75.0 | 66.20 |
| Sodium Lauryl Sulfate (30%) | 0.50–2.50 | 1.00–2.50 | 1.90 |
| Propylene Glycol | 2.0–9.0 | 3.0–6.0 | 5.30 |
| Tetrasodium EDTA | 0.05–0.50 | 0.10–0.30 | 0.15 |
| Part B | | | |
| Lanolin Oil | 5.0–15.0 | 8.0–12.0 | 10.60 |
| Cetyl Alcohol | 3.0–10.0 | 3.5–7.5 | 6.80 |
| Stearyl Alcohol | 1.0–5.0 | 1.0–3.0 | 2.00 |
| Beeswax | 0.50–2.50 | 1.0–2.5 | 1.90 |
| Cod Liver Oil | 1.0–7.0 | 1.0–4.0 | 2.00 |
| BHT | 0.10–1.00 | 0.20–0.80 | 0.50 |
| Part C | | | |
| St. John's Wort Extract | 0.05–0.50 | 0.05–0.15 | 0.10 |
| Witch Hazel Extract | 0.05–0.50 | 0.05–0.15 | 0.10 |
| Chamomile Extract | 0.05–0.50 | 0.05–0.15 | 0.10 |
| Arnica Extract | 0.05–0.50 | 0.05–0.15 | 0.10 |
| Methylparaben | 0.10–0.50 | 0.15–0.40 | 0.30 |
| Propylparaben | 0.10–0.50 | 0.10–0.30 | 0.25 |
| Allantoin | 0.50–2.00 | 0.50–2.00 | 1.50 |
| Fragrance | 0.05–0.50 | 0.10–0.30 | 0.20 |

The Part A ingredients were combined and heated to 175° F. with mixing. The Part B ingredients were combined and heated to 175° F. with mixing. The Part B mixture was then added to the Part A mixture with mixing. The resulting mixture was then cooled to 120° F. with continued mixing. The Part C ingredients were then added with mixing. The final emulsion was allowed to cool with continued mixing. The resulting cream had a pH of 7.4. Samples of the cream prepared from Example 1 were used for accelerated aging stability studies and analyzed for their allantoin concentration after a period of time at 40° C. The results are shown in Table 2.

As can be seen from Table 2, the allantoin in the cream from Example 1 undergoes degradation and would not meet the specifications required for an OTC drug.

TABLE 2

STABILITY OF ALLANTOIN IN SKIN CREAM COMPOSITION OF EXAMPLE 1 WITH STORAGE AT 40° C.

| Days at 40° C. | Weight % Allantoin |
|---|---|
| 0 | 1.5 |
| 30 | 1.4 |
| 60 | 1.3 |
| 90 | 1.2 |

Example 2

Preparation of a Cream Containing Allantoin with Lower pH

An OTC skin cream containing allantoin was prepared using the ingredients in Table 3 to provide a cream with a lower pH.

TABLE 3

COMPOSITION OF ALLANTOIN-CONTAINING SKIN CREAM WITH pH OF 5.3

| INGREDIENT | RANGE | PREFERRED | OPTIMUM |
|---|---|---|---|
| Part A | | | |
| Water | 50.0–90.0 | 55.0–75.0 | 68.68 |
| Sodium Lauryl Sulfate (30%) | 0.50–2.50 | 1.00–2.50 | 1.90 |
| Propylene Glycol | 2.0–9.0 | 3.0–6.0 | 5.30 |
| Tetrasodium EDTA | 0.05–0.50 | 0.10–0.30 | 0.15 |
| Citric Acid | 0.05–0.50 | 0.08–0.35 | 0.12 |
| Part B | | | |
| Lanolin Oil | 5.0–15.0 | 8.0–12.0 | 10.60 |
| Cetyl Alcohol | 3.0–10.0 | 3.5–7.5 | 4.20 |
| Stearyl Alcohol | 1.0–5.0 | 1.0–3.0 | 2.00 |
| Beeswax | 0.50–2.50 | 1.0–2.5 | 1.90 |
| Cod Liver Oil | 1.0–7.0 | 1.0–4.0 | 2.00 |
| BHT | 0.10–1.00 | 0.20–0.80 | 0.50 |
| Part C | | | |
| St. John's Wort Extract | 0.05–0.50 | 0.05–0.15 | 0.10 |
| Witch Hazel Extract | 0.05–0.50 | 0.05–0.15 | 0.10 |
| Chamomile Extract | 0.05–0.50 | 0.05–0.15 | 0.10 |
| Arnica Extract | 0.05–0.50 | 0.05–0.15 | 0.10 |
| Methylparaben | 0.10–0.50 | 0.15–0.40 | 0.30 |
| Propylparaben | 0.10–0.50 | 0.10–0.30 | 0.25 |
| Allantoin | 0.50–2.00 | 0.50–2.00 | 1.50 |
| Fragrance | 0.05–0.50 | 0.10–0.30 | 0.20 |

The Part A ingredients were combined and heated to 175° F. with mixing. The Part B ingredients were combined and heated to 175° F. with mixing. The Part B mixture was added to the Part A mixture with mixing. The resulting mixture was then cooled to 120° F. with mixing at which time the Part C ingredients were added with mixing. The final emulsion was allowed to cool with continue mixing. The resulting cream had a pH of 5.3.

It was found that a similar cream was produced if Part B was added to Part A or Part A was added to Part B. However, the cream has a better appearance if the oil phase and water phase are homogenized under high shear after the two phases are added to one another.

Samples of the cream of this example were used for accelerated aging stability studies and analyzed for their allantoin concentration. The results are shown in Table 4. As can be seen from Table 4, the allantoin is stable over time in a cream with a pH of 5.3.

TABLE 4

STABILITY OF ALLANTOIN IN SKIN CREAM COMPOSITION OF EXAMPLE 2 WITH STORAGE AT 40° C.

| Days at 40° C. | Weight % Allantoin |
|---|---|
| 0 | 1.4 |
| 30 | 1.4 |
| 60 | 1.4 |
| 90 | 1.4 |

ADVANTAGES OF THE PRESENT INVENTION

The present invention provides an allantoin-containing composition that is an oil-in-water emulsion using either beeswax and an anionic emulsifier or a nonionic emulsifier. The composition has improved thermal stability. The composition shows no degradation of allantoin after three months of storage at 40° C. The composition also preserves the desirable properties of the beeswax and emulsifier systems without causing degradation of the allantoin. The composition is suitable for cosmetic and over-the-counter drug uses.

I claim:

1. A composition consisting essentially of an oil-in-water emulsion comprising:
   (a) allantoin; and
   (b) an emulsifier system including beeswax and an anionic emulsifier that is hydrophilic and is soluble in water; and
   (c) an acid to adjust the pH of the emulsion to a value from about 4.5 to about 5.8, the allantoin being stable in the emulsion for at least 90 days at 40° C.

2. A composition comprising an oil-in-water emulsion comprising:
   (a) allantoin;
   (b) an emulsifier system including beeswax and an anionic emulsifier that is hydrophilic and is soluble in water; and
   (c) an acid to adjust the pH of the emulsion to a value from about 4.5 to about 5.8, the allantoin being stable in the emulsion for at least 90 days at 40° C.,
   wherein the anionic emulsifier is selected from the group consisting of ammonium lauryl sulfate, sodium lauryl sulfate, sodium laureth sulfate, sodium oleyl succinate, ammonium lauryl sulfosuccinate, sodium dodecylbenzene sulfate, ammonium laureth sulfate, and sodium lauryl sarcosinate.

3. The composition of claim 2 wherein the emulsifier is sodium lauryl sulfate.

4. The composition of claim 1 wherein the composition comprises at least one organic acid of from 2 to 22 carbon atoms to adjust the pH to from about 4.5 to about 5.8.

5. The composition of claim 4 wherein the composition comprises at least one organic acid selected from the group consisting of citric acid, ascorbic acid, glycolic acid, lactic acid, benzoic acid, and salicylic acid.

6. The composition of claim 1 wherein the composition comprises at least one inorganic acid selected from the group consisting of hydrochloric acid, sulfuric acid, and phosphoric acid to adjust the pH to from about 4.5 to about 5.8.

7. The composition of claim 1 wherein the composition comprises at least one organic acid of from 2 to 22 carbon atoms and at least one inorganic acid selected from the group consisting of hydrochloric acid, sulfuric acid, and phosphoric acid to adjust the pH from about 4.5 to about 5.8.

8. A composition comprising an oil-in-water emulsion comprising:
   (a) allantoin;
   (b) an emollient component comprising:
      (i) lanolin oil;
      (ii) cetyl alcohol;
      (iii) stearyl alcohol;
      (iv) cod liver oil; and
      (v) butylated hydroxytoluene;
   (c) an emulsifier system comprising at least one nonionic emulsifier that is an ethoxylated ether or an ethoxylated ester whose carbon chain length ranges from 8 to 22 carbon atoms and at least one anionic emulsifier; and
   (d) at least one acid selected from the group consisting of:
      (i) an organic acid of from 2 to 22 carbon atoms; and
      (ii) an inorganic acid selected from the group consisting of hydrochloric acid, sulfuric acid, and phosphoric acid to adjust the pH to from about 4.5 to about 5.8, the allantoin being stable in the emulsion for at least 90 days at 40° C.

9. A composition comprising an oil-in-water emulsion comprising:
   (a) allantoin; and
   (b) an emulsifier system including at least one nonionic emulsifier that is an ethoxylated ether or an ethoxylated ester whose carbon chain length ranges from 8 to 22 carbon atoms and at least one anionic emulsifier; and
   (c) an acid to adjust the pH of the emulsion to a value from about 4.5 to about 5.8, the allantoin being stable in the emulsion for at least 90 days at 40° C.

10. The composition of claim 9 wherein the composition comprises at least one organic acid of from 2 to 22 carbon atoms.

11. The composition of claim 10 wherein the composition comprises at least one organic acid selected from the group consisting of citric acid, ascorbic acid, glycolic acid, lactic acid, benzoic acid, and salicylic acid.

12. The composition of claim 9 wherein the composition comprises at least one inorganic acid selected from the group consisting of hydrochloric acid, sulfuric acid, and phosphoric acid.

13. The composition of claim 9 wherein the composition comprises at least one organic acid of from 2 to 22 carbon atoms and at least one inorganic acid selected from the group consisting of hydrochloric acid, sulfuric acid, and phosphoric acid.

14. The composition of claim 1 further comprising an emollient component comprising at least one ingredient selected from the group consisting of lanolin oil, cetyl alcohol, stearyl alcohol, cod liver oil, and butylated hydroxytoluene.

15. The composition of claim 14 wherein the emollient component comprises lanolin oil, cetyl alcohol, stearyl alcohol, cod liver oil, and butylated hydroxytoluene.

16. The composition of claim 9 further comprising an emollient component comprising at least one ingredient selected from the group consisting of lanolin oil, cetyl alcohol, stearyl alcohol, cod liver oil, and butylated hydroxytoluene.

17. The composition of claim 16 wherein the emollient component comprises lanolin oil, cetyl alcohol, stearyl alcohol, cod liver oil, and butylated hydroxytoluene.

18. The composition of claim 1 further comprising St. John's wort extract.

19. The composition of claim 9 further comprising St. John's wort extract.

20. The composition of claim 1 further comprising witch hazel extract.

21. The composition of claim 9 further comprising witch hazel extract.

22. The composition of claim 1 further comprising chamomile extract.

23. The composition of claim 9 further comprising chamomile extract.

24. The composition of claim 1 further comprising arnica extract.

25. The composition of claim 9 further comprising arnica extract.

26. The composition of claim 1 further comprising St. John's wort extract, witch hazel extract, chamomile extract, and arnica extract.

27. The composition of claim 9 further comprising St. John's wort extract, witch hazel extract, chamomile extract, and arnica extract.

28. The composition of claim 1 further comprising a preservative component.

29. The composition of claim 28 wherein the preservative component comprises at least one preservative selected from the group consisting of methylparaben and propylparaben.

30. The composition of claim 9 further comprising a preservative component.

31. The composition of claim 29 where the preservative component is selected from the group consisting of methylparaben and propylparaben.

32. The composition of claim 1 further comprising a chelating agent.

33. The composition of claim 32 wherein the chelating agent is tetrasodium EDTA.

34. The composition of claim 9 further comprising a chelating agent.

35. The composition of claim 35 wherein the chelating agent is tetrasodium EDTA.

36. The composition of claim 1 further comprising a solvent component.

37. The composition of claim 36 wherein the solvent component comprises at least one solvent selected from the group consisting of propylene glycol, butylene glycol, and glycerin.

38. The composition of claim 37 wherein the solvent component is propylene glycol.

39. The composition of claim 9 further comprising a solvent component.

40. The composition of claim 39 wherein the solvent component comprises at least one solvent selected from the group consisting of propylene glycol, butylene glycol, and glycerin.

41. The composition of claim 40 wherein the solvent component is propylene glycol.

42. A composition comprising an oil-in-water emulsion comprising:
   (a) water;
   (b) sodium lauryl sulfate;
   (c) propylene glycol;
   (d) tetrasodium EDTA;
   (e) citric acid;
   (f) lanolin oil;
   (g) cetyl alcohol;
   (h) stearyl alcohol;
   (i) beeswax;
   (j) cod liver oil;
   (k) butylated hydroxytoluene;
   (l) St. John's wort extract;
   (m) witch hazel extract;
   (n) chamomile extract;
   (o) arnica extract;
   (p) methylparaben;
   (q) propylparaben;
   (r) allantoin; and
   (s) fragrance;
where the pH of the composition is from about 4.5 to about 5.8, the allantoin being stable in the emulsion for at least 90 days at 40° C.

43. A composition comprising an oil-in-water emulsion comprising:
   (a) from about 50% to about 90% of water;
   (b) from about 0.5% to about 2.5% of 30% sodium lauryl sulfate;
   (c) from about 2.0% to about 9.0% of propylene glycol;
   (d) from about 0.05% to about 0.50% of tetrasodium EDTA;
   (e) from about 0.05% to about 0.5% of citric acid;
   (f) from about 5% to about 15% of lanolin oil;
   (g) from about 3% to about 10% of cetyl alcohol;
   (h) from about 1% to about 5% of stearyl alcohol;
   (i) from about 0.5% to about 2.5% of beeswax;
   (j) from about 1.0% to about 7.0% of cod liver oil;
   (k) from about 0.1% to about 1.0% of butylated hydroxytoluene;
   (l) from about 0.05% to about 0.50% of St. John's wort extract;
   (m) from about 0.05% to about 0.50% of witch hazel extract;
   (n) from about 0.05% to about 0.50% of chamomile extract;
   (o) from about 0.05% to about 0.5% of arnica extract;
   (p) from about 0.1% to about 0.5% of methylparaben;
   (q) from about 0.1% to about 0.5% of propylparaben;
   (r) from about 0.50% to about 2% of allantoin; and
   (s) from about 0.05% to about 0.50% of fragrance;
the pH of the composition being from about 4.5 to about 5.8, the allantoin being stable in the emulsion for at least 90 days at 40° C.

44. A composition comprising an oil-in-water emulsion comprising:
   (a) from about 55% to about 75% of water;
   (b) from about 1.0% to about 2.5% of 30% sodium lauryl sulfate;
   (c) from about 3.0% to about 6.0% of propylene glycol;
   (d) from about 0.1% to about 0.3% of tetrasodium EDTA;
   (e) from about 0.08% to about 0.35% of citric acid;
   (f) from about 8.0% to about 12.0% of lanolin oil;
   (g) from about 3.5% to about 7.5% of cetyl alcohol;
   (h) from about 1.0% to about 3.0% of stearyl alcohol;
   (i) from about 1.0% to about 2.5% of beeswax;
   (j) from about 1.0% to about 4.0% of cod liver oil;
   (k) from about 0.2% to about 0.8% of butylated hydroxytoluene;
   (l) from about 0.05% to about 0.15% of St. John's wort extract;
   (m) from about 0.05% to about 0.15% of witch hazel extract;
   (n) from about 0.05% to about 0.15% of chamomile extract;
   (o) from about 0.05% to about 0.15% of arnica extract;
   (p) from about 0.15% to about 0.40% of methylparaben;
   (q) from about 0.10% to about 0.30% of propylparaben;
   (r) from about 0.50% to about 2.0% of allantoin; and
   (s) from about 0.1% to about 0.3% of fragrance;
the composition having a pH of from about 4.5 to about 5.8, the allantoin being stable in the emulsion for at least 90 days at 40° C.

45. A composition comprising an oil-in-water emulsion comprising:
   (a) about 68.68% of water;
   (b) about 1.9% of 30% sodium lauryl sulfate;
   (c) about 5.3% of propylene glycol;
   (d) about 0.15% of tetrasodium EDTA;
   (e) about 0.12% of citric acid;
   (f) about 10.6% of lanolin oil;
   (g) about 4.2% of cetyl alcohol;
   (h) about 2.0% of stearyl alcohol;
   (i) about 1.90% of beeswax;

(j) about 2.0% of cod liver oil;
(k) about 0.5% of butylated hydroxytoluene;
(l) about 0.1% of St. John's wort extract;
(m) about 0.1% of witch hazel extract;
(n) about 0.1% of chamomile extract;
(o) about 0.1% of arnica extract;
(p) about 0.3% of methylparaben;
(q) about 0.25% of propylparaben;
(r) about 1.50% of allantoin; and
(s) about 0.20% of fragrance;
the composition having a pH of from about 4.5 to about 5.8, the allantoin being stable in the emulsion for at least 90 days at 40° C.

46. A composition comprising an oil-in-water emulsion comprising:
(a) from about 1.0% to about 2.0% of allantoin; and
(b) an emulsifier system including beeswax and an anionic emulsifier that is hydrophilic and is soluble in water, the pH of the emulsion being from about 4.5 to about 5.8 after the addition of acid to bring the pH into the range of from about 4.5 to about 5.8, the allantoin being stable in the emulsion for at least 90 days at 40° C.

47. A composition comprising an oil-in-water emulsion comprising:
(a) from about 1.0% to about 2.0% of allantoin;
(b) an emollient component comprising:
　(i) lanolin oil;
　(ii) cetyl alcohol;
　(iii) stearyl alcohol;
　(iv) cod liver oil; and
　(v) butylated hydroxytoluene;
(c) an emulsifier system comprising at least one nonionic emulsifier that is an ethoxylated ether or an ethoxylated ester whose carbon chain length ranges from 8 to 22 carbon atoms; and
(d) at least one acid selected from the group consisting of:
　(i) an organic acid of from 2 to 22 carbon atoms; and
　(ii) an inorganic acid selected from the group consisting of hydrochloric acid, sulfuric acid, and phosphoric acid to adjust the pH to from about 4.5 to about 5.8, the allantoin being stable in the emulsion for at least 90 days at 40° C.

48. A composition comprising an oil-in-water emulsion comprising:
(a) from about 1.0% to about 2.0% of allantoin;
(b) an emulsifier system including at least one nonionic emulsifier that is an ethoxylated ether or an ethoxylated ester whose carbon chain length ranges from 8 to 22 carbon atoms; and
(c) an acid to adjust the pH of the emulsion to a value from about 4.5 to about 5.8, the allantoin being stable in the emulsion for at least 90 days at 40° C.

* * * * *